(12) United States Patent
Corvi Mora et al.

(10) Patent No.: US 7,763,282 B2
(45) Date of Patent: Jul. 27, 2010

(54) QUATERNARY COMPOUNDS COMPRISING PROPOLIS AS THE ACTIVE SUBSTANCE

(75) Inventors: Paolo Corvi Mora, Piacenza (IT); Fabio Carli, Trieste (IT); Tiziana Canal, Trieste (IT)

(73) Assignee: Actimex S.R.L., Trieste (IT)

( * ) Notice: Subject to any disclaimer, the term of this patent is extended or adjusted under 35 U.S.C. 154(b) by 228 days.

(21) Appl. No.: 10/537,190

(22) PCT Filed: Dec. 2, 2003

(86) PCT No.: PCT/EP03/13560

§ 371 (c)(1),
(2), (4) Date: Jun. 2, 2005

(87) PCT Pub. No.: WO2004/050063

PCT Pub. Date: Jun. 17, 2004

(65) Prior Publication Data

US 2006/0013891 A1      Jan. 19, 2006

(30) Foreign Application Priority Data

Dec. 2, 2002   (IT) ......................... MI2002A2549

(51) Int. Cl.
*A61K 35/64* (2006.01)
*A61K 31/724* (2006.01)
*A61K 31/704* (2006.01)
*A61K 31/198* (2006.01)
*G01N 33/00* (2006.01)

(52) U.S. Cl. ......................... 424/539; 514/58; 514/559; 514/561; 436/86

(58) Field of Classification Search ...................... None
See application file for complete search history.

(56) References Cited

U.S. PATENT DOCUMENTS

| 3,876,816 | A | * | 4/1975 | Zaffaroni ..................... 426/548 |
| 5,922,324 | A | * | 7/1999 | Aga et al. .................... 424/539 |
| 6,005,100 | A | * | 12/1999 | Mandai et al. ......... 536/123.13 |
| 2003/0104018 | A1 | * | 6/2003 | Bettle et al. ................. 424/401 |
| 2005/0255163 | A1 | * | 11/2005 | Carli et al. .................. 424/489 |

FOREIGN PATENT DOCUMENTS

| EP | 0 109 993 A | | 6/1984 |
| JP | 60188036 A | * | 9/1985 |
| WO | WO 03/097012 A1 | | 11/2003 |

OTHER PUBLICATIONS

Canal, T. "Actimex Srl" <http://www.technoline.area.trieste.it/TenantsData.aspx? IdTenant=67&Action=Data&IdLanguage=2> (accessed Jul. 21, 2008), 5 pages.*
"Physical Constants of Organic Compounds", in CRC Handbook of Chemistry and Physics, 88th Ed. (Internet Version 2008), David R. Lide, ed., CRC Press/Taylor and Francis, §3, 1 page.*

* cited by examiner

*Primary Examiner*—Christopher R Tate
*Assistant Examiner*—Aaron J Kosar
(74) *Attorney, Agent, or Firm*—Nixon Peabody LLP

(57) ABSTRACT

The present invention describes a quaternary composition consisting of propolis delivered in a hydrophilic carrier (cyclodextrin and cyclodextrin derivatives) and co ground with the aid of two compounds for the preparation thereof in the form of a finely divided powder. The composition exhibits advantageous dissolution characteristics in aqueous environments compared to native propolis, hence resulting in greater bioavailability of the active ingredients contained therein.

15 Claims, No Drawings

QUATERNARY COMPOUNDS COMPRISING PROPOLIS AS THE ACTIVE SUBSTANCE

This application is a national stage application under 35 U.S.C. §371 from PCT Application No. PCT/EP2003/013560, filed Dec. 2, 2003.

FIELD OF THE INVENTION

The invention relates to a quaternary composition comprising propolis as the active substance, a delivery carrier and two co-grinding auxiliary compounds, and the use thereof as a dietary supplement or in parapharmaceutical and dermocosmetic products.

STATE OF THE ART

As is known, propolis is a special wax produced by bees which is widely used in phytotherapy as a dietary supplement, since it has no significant side effects and, on the contrary, has been shown to exert beneficial effects in various physiopathological conditions, above all in subjects with immune deficiencies due to causes of various origins.

In addition to immuno-stimulant activities, antibacterial and bacteriostatic activities, antiviral and mycostatic activities, anti-inflammatory and wound healing activities are indeed attributed to propolis.

From the physico-chemical point of view, it appears as a yellow-brown resinous substance with a waxy consistency; indeed it contains resins, balsams, wax, essential oils, pollen, organic substances, mineral salts and oligoelements.

Although it contains many substances peculiar to its plant origin, such as for example terpenes, polysaccharides, uronic and fatty acids, aminoacids, its many curative activities are predominantly attributed to the presence of numerous flavonoid family compounds, amongst which are chrysin, izalpin, galangin, kaempferide, pinobanksin and others, the various therapeutic effects of which have been known for some time and are undergoing a rediscovery.

In view of its nature and the substances contained therein, propolis displays a significant solubility problem and is technologically difficult to handle within the scope of perfecting suitable formulations for its dietary or parapharmaceutical uses.

Indeed, various propolis based preparations are commercially available and mostly in the form of a dried extract or a hydroalcoholic solution. The best raw material however is considered to be the dried extract which is titred in total flavonoids expressed as galangin. The hydroalcoholic solution also finds extensive use, and in this case, it is also usually titred in total flavonoids, expressed as galangin.

In order to solve the problem of the administration of insoluble or poorly soluble active substances, the Applicant has developed a technology which is based on an original, and industrially advantageous co-grinding process of the active substances, with a hydrophilic or hydrophobic carrier and dry co-grinding auxiliary substances (Carli, F. et al. Italian patent No MI2002A001074).

With this process, ternary compositions are obtained, wherein the desired characteristics of amorphisation, solubility and dissolution speed, desired for the purposes of their specific use are conferred to the active substance selected. The process described in the mentioned patent is characterised in that, besides the active substance and a carrier, the co-grinding mixture also comprises a co-grinding auxiliary substance, thus obtaining the desired composition in very shorter grinding times than required for known binary compositions, and under much milder operative grinding conditions.

The process is applicable both with hydrophilic carriers, either linear or cross-linked, such as for example cyclodextrin and cyclodextrin derivatives, dextrans, polyvinylpyrrolidone, cellulose and the derivatives thereof, polyacrylic acids, manno-glucuronans, chitosans, galactomannans and sodium starch glycolate, and with linear and cross-linked hydrophobic carriers (for example ethylcellulose, polymethacrylates, polymethylmethacrylates, and polystyrene and others). As co-grinding auxiliary substances, natural amino acids and derivatives thereof; weak acids, such as for example malic acid, fumaric acid, ascorbic acid, citric acid; polyalcohols and derivatives; chelating agents, such as disodium ethylenediamine tetra acetate; non ionic, anionic or cationic surfactants, as well as lecithins, phospholipids and semisynthetic or synthetic derivatives thereof, may for example be used.

Amino acids, and in particular glycine, lysine, serine, and disodium ethylenediamine tetra acetate are the preferred co-grinding auxiliary substances for this ternary composition process.

The weight ratio between the active substance and carrier is between 1:0.1 and 1:100 and preferably between 1:0.5 and 1:50. The weight ratio between the active substance and the co-grinding auxiliary substance is between 1:0.1 and 1:20 and preferably between 1:0.2 and 1:10.

The co-grinding time is between 0.25 and 24 hours and preferably, the co-grinding time is no greater than 10 hours, and the co-grinding may be carried out using known means (ball mills, knife mills, vibrational mills, centrifugal mills and planetary mills).

The process described in the mentioned patent has various advantages, first of all the possibility of obtaining ternary compositions, comprising an active substance, a hydrophilic or hydrophobic carrier and a co-grinding auxiliary substance wherein the characteristics, such as the solubility, the dissolution speed, the solubilisation kinetics, may be altered to various extent according to the requirements of use. Furthermore, additional advantages are represented by the catalysing effect of the co-grinding auxiliary substance, which is also effective in the hydrophilic drug/hydrophobic carrier combination and still by the fact that, being able to use lower energy levels and or shorter grinding times, the process may also be used for substances which are poorly stable from the physico-chemical point of view, for example thermolabile substances.

Propolis, as already mentioned, is normally used for the most part as a dietary supplement, either in its dry extract or hydroalcoholic solution forms, however in both cases it has certain application problems, due to its poor solubility in aqueous environments, but also to its poor lipophilicity, which influences the bioavailability of the active ingredients contained therein.

SUMMARY OF THE INVENTION

The Applicant has now surprisingly found that compositions in the form of finely divided dried powders, characterised by being quaternary and by comprising propolis as the active substance, a hydrophilic carrier and two co-grinding auxiliary substances, one of which is an aminoacid and the other is a sweetening agent, glycyrrhizate, have greater solubility than the corresponding ternary compositions, where the sole auxiliary substance is constituted by aminoacids.

Accordingly, the object of the present invention are said quaternary compositions, comprising propolis as the active substance, and the use thereof for the preparation of dietary supplements or parapharmaceutical and dermocosmetic products, either as such or with appropriate excipients or diluents.

DETAILED DESCRIPTION OF THE INVENTION

The characteristics and the advantages of the composition according to the present invention will be illustrated by the following detailed description.

By using the process already mentioned previously, and described in the Italian patent No MI 2002A001074 for the preparation of ternary compositions, the Applicant has surprisingly found that the addition of a fourth substance, which is usually used as a sweetening agent, leads to an advantage in terms of solubility with respect to the ternary compositions which do not contain it.

Indeed, this unexpectedly behaves as a second co-grinding auxiliary substance, surprisingly improving the characteristics of the composition itself. In particular the quaternary composition, object of the invention, may have the following characteristics.

For the quaternary composition comprising propolis, linear or cross-linked hydrophilic carriers, such as for example cyclodextrin and cyclodextrin derivatives, and aminoacid auxiliary substances, preferentially selected from the group consisting of glycine, glutamic acid, lysine and serine are preferred.

The weight ratio between the active substance and the carrier may be between 1:1 and 1:20 and preferably between 1:5 and 1:8.

The weight ratio between the active substance and the aminoacid co-grinding auxiliary substance may between 1:0.1 and 1:2 and preferably between 1:0.2 and 1:1.

The ratio between the active substance and the second glycyrrhizate co-grinding auxiliary substance may be between 1:0.5 and 1:2 and preferably 1:1.

The co-grinding time for the preparation of the quaternary composition is usually very short and comprised of between 0.30 and 2.0 hours.

The following experimental examples are given as non-exhaustive illustration of the present invention.

Example 1 A Quaternary Composition with Propolis, Ammonium Glycyrrhizate, β Cyclodextrin and L-Glycine 2 Kg of highly-purified propolis extract, ammonium glycyrrhizate, β cyclodextrin and L-glycine mixture, in the ratio of 1:1:7.5:0.5 w/w, are homogenised for 10 minutes in a rotating body powder mixer. The mixture is loaded into a vibrational mill equipped with sintered alumina cylindrical milling means and subjected to grinding with a vibrational amplitude comprised of between 6 and 10 mm for 1 hour.

The product obtained, with a yield of 98.9%, is sieved and 99.8% of the product recovered in the form of a finely divided, free-flowing powder.

Example 2 A Quaternary Composition with Propolis, Ammonium Glycyrrhizate, β Cyclodextrin and Glutamic Acid 2 Kg of highly-purified propolis extract, ammonium glycyrrhizate, β cyclodextrin and glutamic acid mixture in a ratio of 1:1:7.5:0.5 w/w, are homogenised per 10 minutes in a rotating body powder mixer. The mixture is loaded into a vibrational mill equipped with sintered alumina cylindrical milling means and subjected to grinding with a vibrational amplitude comprised of between 6 and 10 mm for 1 hour.

The product obtained, with a yield of 98.9%, is sieved and 99.8% of product recovered in the form of a finely divided free-flowing powder.

The quaternary compositions described may be replicated using, as the aminoacid co-grinding auxiliary, substance, other aminoacids amongst which are lysine and serine.

With the aim of comparing the quaternary mixture of examples 1 and 2, ternary compositions have also been prepared without the second ammonium glycyrrhizate co-grinding auxiliary substance, in accordance with the following examples 3 and 4.

Example 3 A Ternary Composition with Propolis, β Cyclodextrin and L-Glycine

1 Kg of highly-purified propolis extract, β cyclodextrin and L-glycine mixture in a ratio of 1:7.5:0.5 w/w, are homogenised for 10 minutes in a rotating body powder mixer. The mixture is loaded into a vibrational mill equipped with sintered alumina cylindrical milling means and subjected to grinding with a vibrational amplitude comprised of between 6 and 10 mm for 1 hour.

The product obtained, with a yield of 97.8%, is sieved and 99.6% of product recovered in the form of a finely divided free-flowing powder.

Example 4 A Ternary Composition with Propolis, β Cyclodextrin and Glutamic Acid 1 Kg of highly-purified propolis extract, β cyclodextrin and glutamic acid mixture in a ratio of 1:7.5:0.5 w/w, are homogenised for 10 minutes in a rotating body powder mixer. The mixture is loaded into a vibrational mill equipped with sintered alumina cylindrical milling means and subjected to grinding with a vibrational amplitude comprised of between 6 and 10 mm for 1 hour.

The product obtained, with a yield of 97.8%, is sieved and 99.6% of product recovered in the form of a finely divided free-flowing powder.

The compositions of the examples 1, 2, 3 and 4 have then been compared with the starting raw material with regard to their solubilities, obtaining the results reported in the following table 1.

TABLE 1

| Compositions | solubility | Increase |
| --- | --- | --- |
| A-Propoflavis raw material | 465 µg/ml | |
| B-example 3 | 1695 µg/ml | 3.6 fold over A |
| C-example 1 | 2430 µg/ml | 5.2 fold over A |
| | | 1.4 fold over B |
| D-example 4 | 1584 µg/ml | 3.4 fold over A |
| C-example 2 | 1999 µg/ml | 4.3 fold over A |
| | | 1.3 fold over B |

From the results shown above, it is clearly evident that the ternary composition containing an aminoacid co-grinding substance causes a significant improvement in the solubility of the native propolis, but that with the addition of the second co-grinding substance—ammonium glycyrrhizate—the solubility increases further by a range comprised of between 30 and 40% with respect to the corresponding ternary composition. Such results in themselves are very significant in that it is apparent to any expert in the art that an increase in solubility, even by less than that found, may have an important and positive reflection on the bioavailability of the active ingredient(s) contained within the active substance.

The quaternary compositions obtained in powder form, according to the present invention, may be formulated into products adapted for being used as dietary supplements or as parapharmaceutical, Including dermocosmetic, products. For the uses as dietary supplements and parapharmaceutical, the quaternary compositions, forming the object of the present invention, may be formulated in the form of powders, even in single dose sachets, either as such or admixed with dietary or pharmaceutically acceptable excipients and diluents. Furthermore, they may also be used in different forms, such as for example capsules, tablets, pastes, gels, solutions or suspensions and sprays, both as such and admixed with dietary or pharmaceutically acceptable excipients adapted to such other forms. Furthermore for the dermocosmetic use the quaternary compositions, forming the object of the present invention, may be formulated cosmetic acceptable excipients as lotions, creams, ointments, pastes, gels, stick and other topical forms known for this use.

| Example 5 lip cream 2% | |
|---|---|
| Components | % |
| Purified water | 64.75 |
| Vaseline oil | 12.0 |
| Dermoil HDE | 5.0 |
| Arlacel P135 | 3.5 |
| Atlas G-2330 | 2.0 |
| Vegetable Glycerine | 3.0 |
| Cutin HR | 2.5 |
| C-Proflavis (example 1) | 2.0 |
| Beeswax | 1.1 |
| Polyglyceryl-3 beeswax | 2.0 |
| Euxil K 300 | 0.8 |
| Mg stearate | 0.5 |
| Allantoin | 0.2 |
| Karitè butter | 0.2 |
| Vitamin E acetate | 0.2 |
| All fruit flavour | 0.15 |
| BHT | 0.05 |
| EDTA disodium | 0.05 |

| Example 6 oral cavity spray 3% | |
|---|---|
| Water | 92.91 |
| C-Proflavis (example 1) | 3.0 |
| Menthol clathrate | 1.0 |
| Carbopol 934 | 0.30 |
| 30% simethicone emulsion | 2.0 |
| Sodium hydrate 18% | 0.69 |
| Methyl p-hydroxyibenzoate | 0.09 |
| Propyl p-hydroxyibenzoate | 0.01 |
| | 100 |

| Example 7 chewable tablets | |
|---|---|
| Componentis | mg |
| Biomaltodextrines | 529.0 |
| Destrates | 210.0 |
| Peppermint flavour | 72.0 |
| C-Proflavis (example 1) | 50.0 |
| Technological excipients | 27.0 |
| Mix biovegetable flavours | 7.0 |

| Example 8 chewable tablets | |
|---|---|
| Biomaltodextrines | 536.0 |
| Destrates | 210.0 |
| Apple flavour | 65.0 |
| C-Proflavis (example 1) | 50.0 |
| Technological excipients | 27.0 |
| Mix biovegetable flavours | 7.0 |

| Example 9 chewable tablets | |
|---|---|
| Biomaltodextrines | 536.0 |
| Destrates | 210.0 |
| Wood fruit flavour | 65.0 |
| C-Proflavis (example 1) | 50.0 |
| Technological excipients | 27.0 |
| Mix biovegetable flavours | 7.0 |

| Example 10 chewable tablets | |
|---|---|
| Biomaltodextrines | 536.0 |
| Destrates | 210.0 |
| Milk/honey flavour | 55.0 |
| C-Proflavis (example 1) | 50.0 |
| Technological excipients | 27.0 |
| Mix biovegetable flavours | 17.0 |

| Example 11 chewable tablets | |
|---|---|
| Biomaltodextrines | 370.5 |
| Destrates | 375.5 |
| Cola flavour | 55.0 |
| C-Proflavis (example 1) | 50.0 |
| Technological excipients | 27.0 |
| Mix biovegetable flavours | 17.0 |

| Example 12 chewable tablets | |
|---|---|
| Biomaltodextrines | 506.0 |
| Destrates | 255.0 |
| Citrus flavour | 40.0 |
| C-Proflavis (example 1) | 50.0 |
| Technological excipients | 37.0 |
| Mix biovegetable flavours | 7.0 |

| Example 13 effervescent tablets | |
|---|---|
| Actvive principles | mg |
| Spirea ulmaria/β cyclodextrin | 100.0 |
| C-Proflavis (example 1) | 50.0 |
| Rosa canina dried extract | 50.0 |
| Excipients | mg |
| Anhydrous citric acid | 2000.0 |
| Sodium bicarbonate | 600.0 |
| Sodium carbonate | 600.0 |
| Sorbitol | 340.3 |
| E162 | 160.0 |
| Orange flavour | 50.0 |
| Red orange dried extract 10% | 25.0 |
| Acesulfame K | 20.0 |
| Polisorbate 20 | 2.0 |
| Dimethicone emulsion 10% | 2.0 |
| Vitamin $B_2$ | 0.7 |

The invention claimed is:

1. A quaternary co-ground powdered composition consisting essentially of propolis, as an active substance; a hydrophilic carrier selected from the group consisting of cyclodextrins; and two co-grinding auxiliary substances, of which one is an amino acid and one is glycyrrhizate, said composition having a greater aqueous solubility than the corresponding ternary composition having a sole auxiliary substance, wherein the sole auxiliary substance consists of an amino acid.

2. The composition of claim 1 wherein the amino acid auxiliary substance is an amino acid selected from the group consisting of glycine, glutamic acid, lysine, and serine.

3. The composition of claim 1 wherein the weight ratio between the active substance and the carrier is between 1:1 and 1:20.

4. The composition of claim 3 wherein the weight ratio between the active substance and the carrier is between 1:5 and 1:8.

5. The composition of claim 1 wherein the weight ratio between the active substance and the amino acid auxiliary substance is between 1:0.1 and 1:2.

6. The composition of claim 5 wherein the weight ratio between the active substance and the amino acid auxiliary substance is between 1:0.2 and 1:1.

7. The composition of claim 1 wherein the weight ratio between the active substance and the second glycyrrhizate co-grinding auxiliary substance is between 1:0.5 and 1:2.

8. The composition of claim 7 wherein the weight ratio between the active substance and the glycyrrhizate co-grinding auxiliary substance is 1:1.

9. A quaternary co-ground powdered composition consisting essentially of propolis, as an active substance; a hydrophilic carrier selected from the group consisting of cyclodextrins; and two co-grinding auxiliary substances of which one is an amino acid selected from the group consisting of glycine, glutamic acid, lysine, and serine and one is glycyrrhizate, wherein in said composition the weight ratios among the propolis active substance, the hydrophilic carrier, the amino acid, and the glycyrrhizate are 1:7.5:0.5:1.

10. A mixture comprising the composition of claim 1 combined with suitable excipients or diluents or combination thereof for preparation of products for use as dietary supplements.

11. A mixture comprising the composition of claim 1 combined with suitable excipients or diluents or combination thereof for preparation of products for parapharmaceutical use.

12. A mixture comprising the composition of claim 1 combined with suitable excipients or diluents or combination thereof for preparation of products for dermocosmetic use.

13. The mixture of claim 12 wherein said products are selected from the group consisting of powders, lotions, creams, ointments, pastes, gels, and stick.

14. The mixture of claim 10 wherein said products are selected from the group consisting of powders, capsules, tablets, pastes, gels, solutions and suspensions.

15. The mixture of claim 11 wherein said products are selected from the group consisting of powders, capsules, tablets, pastes, gels, solutions, suspensions and spray.

* * * * *